United States Patent [19]
Purkait

[11] Patent Number: 5,941,909
[45] Date of Patent: Aug. 24, 1999

[54] FILLING MATERIAL FOR SOFT TISSUE IMPLANT PROSTHESES AND IMPLANTS MADE THEREWITH

[75] Inventor: Bobby Purkait, Montecito, Calif.

[73] Assignee: Mentor Corporation, Santa Barbara, Calif.

[21] Appl. No.: 08/908,732

[22] Filed: Aug. 7, 1997

Related U.S. Application Data

[63] Continuation-in-part of application No. 08/389,751, Feb. 14, 1995, Pat. No. 5,658,329.

[51] Int. Cl.$^6$ .......................................................... A61F 2/02
[52] U.S. Cl. ........................................ 623/11; 623/7; 623/8
[58] Field of Search ........................................ 623/7, 8, 11

[56] References Cited

U.S. PATENT DOCUMENTS

| | | |
|---|---|---|
| 4,657,553 | 4/1987 | Taylor . |
| 4,731,081 | 3/1988 | Tiffany et al. . |
| 4,749,585 | 6/1988 | Greco et al. . |
| 4,772,284 | 9/1988 | Jefferies et al. . |
| 4,787,905 | 11/1988 | Loi . |
| 4,995,885 | 2/1991 | Morawietz . |
| 5,007,940 | 4/1991 | Berg . |
| 5,067,965 | 11/1991 | Ersek et al. . |
| 5,116,371 | 5/1992 | Christensen et al. ...................... 623/11 |
| 5,219,360 | 6/1993 | Georgiade . |
| 5,282,857 | 2/1994 | Perry et al. . |
| 5,287,857 | 2/1994 | Mann . |
| 5,340,352 | 8/1994 | Nakanishi et al. . |
| 5,344,451 | 9/1994 | Dayton . |
| 5,376,117 | 12/1994 | Pinchuk et al. . |
| 5,658,329 | 8/1997 | Purkait ...................................... 623/11 |
| 5,662,708 | 9/1997 | Hayes et al. ................................ 623/11 |
| 5,798,096 | 8/1998 | Pavlyk . |

FOREIGN PATENT DOCUMENTS

| | | |
|---|---|---|
| 0 186 430 | 7/1986 | European Pat. Off. . |
| 0 338 813 | 10/1989 | European Pat. Off. . |
| 0 575 035 | 12/1993 | European Pat. Off. . |
| 2667539 | 6/1991 | France . |
| 2691068 | 11/1993 | France . |
| 2693901 | 1/1994 | France . |
| 2707499 | 1/1995 | France . |
| WO93/00867 | 1/1993 | WIPO . |
| WO93/20780 | 10/1993 | WIPO . |
| WO93/22987 | 11/1993 | WIPO . |
| WO94/07434 | 4/1994 | WIPO . |
| WO94/25078 | 11/1994 | WIPO . |

OTHER PUBLICATIONS

"An In Vivo Study of the Effect of Various Breast Implant Filler Materials on Mammography", Neal Handel et al., Plastic and Reconstructive Surgery, vol. 91, No. 6, May 1993.

"Hyaluronic Acid–Filled Mammary Implants: An Experimental Study", Kant Lin et al., Plastic and Reconstructive Surgery, vol. 94, No. 2, Aug. 1994.

*Primary Examiner*—Paul B. Prebilic
*Attorney, Agent, or Firm*—Blakely, Sokoloff, Taylor & Zafman LLP

[57] ABSTRACT

A new soft tissue implant filling material is disclosed. The surgically implantable soft tissue implant filling material has good aesthetic properties, as measured by viscosity and elasticity, and good elimination properties. One embodiment of such a new filling material is a gel which comprises three components. The first component is a water soluble polymer or hydrogel that has a high molecular weight. Alternatively, the first component is both crosslinked and has a high molecular weight. The second component of the filling material is a water-soluble polymer that is eliminated rapidly through the kidneys upon subcutaneous release. The third component of this filling material is saline, which is used to dissolve the polymer and to adjust the osmolality of the polymer. In addition, a buffer may be added to the filling material to adjust the pH of the gel. One gel formulation of the present invention, in its preferred embodiment, consists of polyacrylamide and derivatives thereof.

14 Claims, No Drawings

FILLING MATERIAL FOR SOFT TISSUE IMPLANT PROSTHESES AND IMPLANTS MADE THEREWITH

BACKGROUND OF THE INVENTION

The present application is a continuation-in-part of U.S. patent application Ser. No. 08/389,751, entitled "Filling Material for Soft Tissue Implant Prostheses and Implants made therewith" filed Feb. 14, 1995, which issued Aug. 19, 1997 as U.S. Pat. No. 5,658,329.

FIELD OF THE INVENTION

The present invention is directed to the field of soft tissue implant prostheses, such as breast and testicular implants and tissue expanders, and more specifically, is directed to a filling material for such implants.

ART BACKGROUND

Soft tissue medical implants generally are made of a silicone medical grade elastomer shell and a filling material disposed inside of the shell. If the shell ruptures, either as a result of accidents or through crease-fold flaw or failure, the filling material escapes into the body. For this reason, if the filling material is a gel it is desirable that the gel contain only biocompatible ingredients, have a low total solids content, be excretable or metabolizable and be sterile.

Soft tissue medical implants, such as breast implants, testicular prostheses, chin, cheek, pectoral and calf implants and the like, but particularly, breast implants, have gone through a tremendous transition over the past few years as a result of various concerns, justified or not, regarding the safety of silicone gel filling materials. As a result, a number of materials have been proposed to replace the silicone gel materials which have been commonly used over the past 30 years, or longer.

For example, in U.S. Pat. No. 4,731,081 a number of materials including polyvinylpyrrolidone (PVP), polyvinyl alcohol, hydroxyethyl starch, lecithin, peanut oil, cottonseed oil, fatty acid salts and fatty acid esters have been proposed to prevent the problem of fold flaw.

U.S. Pat. No. 4,772,284 relates to a breast implant filled with collagen gel or a gel made from polyalpha amino homopolymers or random copolymers having a molecular weight in the range of 5,000 to 400,000.

U.S. Pat. No. 4,787,905 relates to a gel for a breast prosthesis consisting of a mixture of hydroxy-terminated polybutadiene resin, diundecylphthalate, polymethylenepolyphenyl isocyanate and dibutylin dilaurate catalyst which cures to form a gel.

U.S. Pat. No. 4,995,885 relates to an implant with alleged radiolucent characteristics made from biocompatible triglycerides, such as peanut oil or sunflower oil, having an effective atomic number of 5.9.

U.S. Pat. No. 5,287,857 relates to an implant with a gel filling material of water and a cellulose gelling agent, such as carboxymethylcellulose, methylcellulose, hydroxyethylcellulose, or the like. A lubricating agent additive is also proposed.

U.S. Pat. No. 5,219,360 relates to a filling material for an implant comprising a gel made of cross-linked hyaluronic acid and hylan.

No one has heretofore proposed that alginate gel may be used as a filling material. There is a significant amount of research on alginate materials, which will be discussed briefly herein. In molecular terms, alginates constitute a family of unbranched copolysaccharides of 1–4 linked β-D-mannuronic acid (M) and -L-guluronic acid (G), of composition and sequence dependent on the organism or tissue form which they are isolated. In seaweed alginates, such as that isolated from *Laminaria hyperborea,* the two monomers are arranged in a pattern of blocks along the chain, with homopolymeric regions (termed M and G blocks) interspersed with regions of alternating structure (MG blocks).

It is the G-blocks of alginates which impart one of its most useful and important properties, namely, the ability of alginic acid to form water insoluble salts by electrostatic interactions with some multivalent ions (e.g., $Ca^{2+}$, $Ba^{2+}$, $Al^{3+}$). Divalent cations, such as calcium, bind preferentially to G-blocks in a highly cooperative manner that has been termed the "egg-box model". Homogeneous alginate emulsions can be made using $CaCl_2$ or other calcium salts in combination with ethanol, and phosphatidylcholine. Pronova Biopolymers, Inc. has recently begun promoting some highly purified alginates designed for certain biomedical applications. More specifically, the company produces ultra-pure grades with a very low content of protein, endotoxin, heavy metals and polyphenols. The company supplies alginates from *Laminaria hyperborea,* a seaweed naturally high in G content, which have been shown not to stimulate cytokine (e.g., IL-6, TNF- ) production when incubated with monocytes.

George Blaine, in 1944, is credited with first illustrating that calcium/sodium alginate is resorbable in animals. Histologically, resorption usually occurs by phagocytosis in the absence of a dense inflammatory capsule, necrosis, fibrosis or scar tissue formation. Alginates are listed as non-irritants to human skin and eyes in the most recent BIBRA Toxicology Report. Extensive testing has established that alginate is safe when used in a body.

Clinically, Oliver and Blaine, in 1949, used alginate as an absorbable hemostat in various types of brain surgery. Since the 1940's alginate has been used successfully in other deep surgeries, as an intravenous plasma expander, for intraperitoneal and subcutaneous injections of various drugs, in various surgeries of the eye, ear, nose, mouth, throat and sinuses, as a hemostat for ulcers of the gastrointestinal tract, in morphine rectal suppositories and medical examinations of the colon, rectum and vagina, as wound, burn and surgical dressings, for ileostomal impressions, and even to correct ingrown toe-nails.

None of these prior art patents recognize or address most of the important technological issues which are involved in the selection of an appropriately safe and effective implant filling material. It would be desirable to provide a new filling material which is safe and effective and is an improvement over the characteristics of the prior art materials.

To date, no known filler has the optimized properties of both good aesthetics and rapid elimination of a large majority of the filling material. Some of the aforementioned materials, such as silicon gel, have good aesthetic properties. However, they also exhibit marginally acceptable elimination properties. Other fillers, such as saline, oils and low molecular weight polymers like PVP, have acceptable elimination properties while providing minimal aesthetics.

Accordingly, it is desirable to provide a new filling material which is safe and effective, and which also provides optimized and balanced aesthetic and elimination properties.

SUMMARY OF THE INVENTION

The present invention is a tissue implant filling material having good aesthetic properties, as measured by viscosity and elasticity, and good elimination properties, for use in surgically implantable soft tissue implants.

One embodiment of such a new filling material is a gel which comprises three components. The first component is a water soluble polymer or hydrogel that has a high molecular weight. Alternatively, the first component may be both crosslinked and have a high molecular weight. The second component of the filling material is a water-soluble polymer that is eliminated rapidly through the kidneys upon subcutaneous release. The third component of this filling material is saline, which is used to dissolve the polymer and to adjust the osmolality of the polymer. In addition, a buffer may be added to the filling material to adjust the pH of the gel.

One gel formulation of the present invention, in its preferred embodiment, consists of polyacrylamide and derivatives thereof.

DETAILED DESCRIPTION OF THE PREFERRED EMBODIMENT

The materials of the present invention have the following particularly advantageous characteristics:

1) Compatibility with the shell or membrane: The filling material must necessarily be compatible with the shell material in that it cannot react with the shell, and the shell must be capable of retaining the filling material without substantial leakage or bleeding. There shall be no degradation of shell or membrane physical properties and other components (e.g., valves, patches, washers) due to contact with filling material. The standard shell materials typically used in medical implants include polydimethyl siloxane, polyurethane, polyurethane/polyester copolymer, or other similar viscoelastic membranes. One test for bleed of the filling material through the shell involves the solubility of the filling material in the shell material, or the measurement of the Hildebrand parameter, which is a measure of polymer-liquid interaction at the interface between the filler and the shell. For non-aqueous filling materials, the Hildebrand parameters of the filling material and the shell or membrane should be sufficiently different to discourage bleed. A high molecular weight of the filling material will also discourage bleed.

2) Viscosity and molecular weight: These parameters relate to the feel of the prosthesis, making the preferred filling material more gel-like than liquid-like. Additionally, it is necessary to provide both chemical and mechanical stability so that the filling material does not lose its soft tissue-like feel either during storage or in the body at body temperature. For the purposes of the present invention, an appropriate balance between viscosity and isotonicity, which is related to the molecular weight and the solids content, on the one hand, and biocompatibility of the material, which is a function of its excretability, ability to be metabolized, and its long-term toxicology effects, on the other hand, is important in the selection of an appropriate filling material.

3) Sterility: The material must be sterilizable by heat or radiation or chemical or filtration methodology, and should be compatible with appropriate antimicrobial additives. Several antimicrobial and antifungal agents which are shown to be effective include ceftazidime or other third generation cephalosporins, miconazole and amphotericin B.

4) Osmolality: The osmolality should be in the range of 200 to 400 mOsm/kg.

5) pH: The pH should be in the range of pH 6 to 8.

6) Buffering: An appropriate buffer may be added and should be compatible with the material to maintain the appropriate pH and stability of the filling material.

7) Antioxidants: Appropriate antioxidants, such as $MgCl_2$, may be added to enhance the stability of the formula.

8) Lubricity: Lubricity agents may be added to improve the ability of the filling material to protect the envelope from abrasion.

9) Radiolucency: The radiolucency of the filling material should be comparable with or better than that of 0.9% saline.

10) Biocompatibility: The material should be biocompatible. As used herein biocompatibility means that the material is either excreted from the body, or is easily metabolized into harmless byproducts. Non-metabolized materials must be sufficiently small that they can be transported through membranes and excreted by the body in the urine or fecal matter. Overall, the material should not demonstrate any long-term adverse affect.

Several ideal compositions have been identified and their formulations are set forth below:

ALGINATE

A calcium alginate gel is a presently desired form of the filling material, and is made by combining sodium alginate with calcium chloride or other calcium salts in an appropriate ratio. The composition consists of the following components:

Sodium alginate: 0.25% to 15% and preferably, 1 to 5%, and most preferably, 2%

Calcium chloride dihydrate ($CaCl_2.2H_2O$): 0.1% to 1.2%, and preferably 0.2% to 0.5%, and most preferably 0.32%.

PC (phosphatidylcholine): 0.001% to 0.5%, preferably 0.005% to 0.15%, and most preferably 0.01%.

Sodium Chloride: 0.2% to 0.5% to make the formulation isotonic.

Ethanol: 0.1% to 8%, preferably 0.5% to 5%.

The osmolality range for the final alginate gel is 200 mOsm/kg to 400 mOsm/kg, and preferably 250 mOsm/kg to 350 mOsm/kg.

The viscosity of the alginate gel is in the range of 5,000 cP to 150,000 cP, and preferably 50,000 cP to 120,000 cP as measured by a Brookfield model DV-II+ viscometer at and a shear rate of 0.42 $sec^{-1}$.

The pH of the final alginate gel is broadly in the range of 5 to 10, and preferably 6 to 8.

The alginate has a guluronic acid content above 30%. Also, bacterial alginate which has been modified with a mannuronic acid epimerase would fulfill the necessary characteristics of an appropriate alginate material.

In the presently preferred formulation, the calcium alginate gel is formed by mixing five solutions of low viscosity together:

1) Solution I: A mixture of 13 volume % of (a) and 87 volume % of (b). Note: The solution will have a blue hue; but no precipitation occurs.
   (a) 0.77 g of PC in 100 ml of EtOH;
   (b) 0.9 wt % $CaCl_2.2H_2O$ in USP water for injection;
2) Solution II: USP water for injection;
3) Solution III: 3.33 wt % sodium alginate and 1.0 wt % NaCl in USP water for injection;
4) of Solution IV: USP water for injection;
5) Solution V: 1.1 wt % $CaCl_2.2H_2O$ in USP water for injection.

These solutions are preferably filtered through a 0.2μ filter and filled into mammaries in the following way (for every 100 ml of calcium alginate gel):

(1) Filter 11.5 ml of Solution I into each mammary using filter #1.

(2) Filter 5 ml of Solution II into each mammary using filter #1.

(3) With as little agitation as possible, filter 60 ml of Solution III into each mammary using filter #2. After each mammary is filled, mix the solution rather vigorously by massaging the mammary with hands for about 45 seconds.

(4) Filter 5 ml of Solution IV into each mammary using filter #1. Mix to form a homogeneous solution.

(5) Filter enough air into each mammary so that the contents of the mammary are well below the fill tube inlet opening.

(6) With as little agitation as possible, filter 2.0 ml of Solution V to each mammary 1 using filter #1 (see footnote [1]) After each mammary is filled, mix the solution rather vigorously by massaging the mammary with hands until the solution becomes homogeneous. The solution should thicken quickly. Continue massaging each mammary for an additional 30 seconds.

[1] Mixture splashing back to the inlet will result in gel formation and blockage of the opening. If blockage should occur, try massaging the inlet opening area. Do not apply high pressure to a blocked inlet, since it may result in a separation of the fill tube component.

The mammary prostheses are then packaged into double thermoforms with lids or pouches after the fill valve is sealed with a silicone adhesive. This package is shipped inside a zip-lock bag (to provide moisture barrier) for terminal sterilization. Electron beam irradiation, gamma irradiation or autoclave may be used to terminal sterilize the package after removing it from the zip-lock bag. The package is then be placed into a foil pouch and sealed up.

Phosphatidylcholine (PC) is a desired component of the gel. It provides several different functions. PC is amphiphilic, thus, it is a lubricity agent for the silicone rubber shell. PC also competes with the alginate chains for calcium cations, transforming a calcium alginate brittle gel into a flowing gel. This property is consistent with previous uses of PC as a gel dispersant and is believed to aid in excretion of large quantities of the gel should the shell rupture. PC acts as an emulsifier, which has been shown to increase both polysaccharide and cephalosporin stability. The compatibility of alginate with PC has been established in other systems such as microencapsulated liposomes, wound dressings and transdermal controlled release systems.

PC has been used clinically in parenteral preparations of doxorubicin, amphotericin, benzodiazepines, penicillin, and vitamins as well as an emulsifier for essential fatty acids and oils in total parenteral nutrition.

For the use of an alginate filling material in an inflatable prosthesis, it may be desirable to incorporate antimicrobial and antifungal agents. Although alginates are very resistant to bacteria when compared to other polysaccharides, some microorganisms do produce alginases. Bacterial and fungal growth studies were performed using the most commonly encountered bacteria and fungi in the operating rooms of hospitals. The study concluded that 0.06% ceftazidime and 0.008% miconazole produced a three (3) or more log reduction in the population of all the challenging organisms. Miconazole is a broad spectrum antifungal, that also has activity against gram-positive bacteria. In addition, the mentioned concentration of ceftazidime is higher than the minimal inhibitory concentration of all reported ceftazidime resistant strains; however, should simultaneous rupture of 2–800 cc implants occur, the amount of ceftazidime and miconazole released would be lower than a single prophylactic intravenous or intramuscular dose, and therefore, the amounts of antibiotics used in the present invention are believed to be safe.

The literature contains several citations involving the use of intraluminal steroids, antimicrobials, anti-inflammatories and pain relievers. To date, hundreds of thousands of patients have received hip or knee prostheses fixed with antibiotic containing cement. It has also become clinically routine to impregnate vascular grafts or catheter cuffs with antibiotics.

A polar steroid such as cortisol has a permeation value for silicone rubber of 0.00025 $\mu$g mm$^{-1}$h$^{-1}$. PC, miconazole and ceftazidime have been chosen with polar groups and molecular weights greater than steroids (330–450 Da.), so that migration through the shell should be negligible.

All sterilization methods investigated, with the exception of filtration, cause depolymerization of alginate. Using free radical scavengers can enhance the stability of the alginate solution to electron beam irradiation, gamma irradiation or autoclave. Testing showed that the gel with 6% glycerol or mannitol, or 0.5 to 5% ethanol maintained an acceptable viscosity after irradiation or autoclave.

SODIUM HYALURONATE 1. 1 to 10% hyaluronic acid with modified balanced salts (USP or NF grade): 0.075% KCl, 0.048% $CaCl_2$, 0.030% $MgCl_2$, and NaCl in sterile pyrogen-free water to achieve the osmolality range specified below. ($MgCl_2$ also serves as an antioxidant agent.)

2. 0.03 to 0.13% Ceftazadime and 0.002 to 0.05% miconazole.

3. The viscosity of the hyaluronic acid gel is 5,000–150,000 cps at 37° C. and the osmolality is 200 to 400, and preferably 250–350 mOsm/kg.

PVA 3A. 6% polyvinyl alcohol (PVA) (M.W. equivalent to Elvanol 52-22; 40 KD) with 0.07 ml of 25% glutaraldehyde (cross-linking agent), 0.3 ml 85% $H_3PO_4$, 4 ml 1.85M NaOH per 100 ml of 6% PVA solution and 0.66% NaCl in sterile pyrogen-free water.

or 3B. 3% PVA (M.W. equivalent to Elvanol 50-42; 75 KD) with 0.06 ml of 25% glutaraldehyde (cross-linking agent), 0.3 ml 85% $H_3PO_4$, 4 ml 1.85M NaOH per 100 ml of 6% PVA solution and 0.66% NaCl in sterile pyrogen-free water.

or 3C. 10% PVA (M.W. equivalent to Elvanol 52-22; 40 KD) and 0.66% NaCl in sterile pyrogen-free water buffered to pH 7 with 0.05M $NaH2PO_4$.

or 3D. 2 to 30% PVA synthesized from Ethanol based Solvent (MW range 10–50 KD) with similar combination of crosslinking agent, buffering and stability agents as previously discussed in 3A, 3B or 3C.

The molecular weight which provides an appropriate viscosity for PVA is preferably in the range of 10,000 to 40,000 Daltons.

HPMC

Hydroxypropylmethyl cellulose (HPMC) and its derivatives may be employed as filling materials in the present invention. Derivatives of HPMC include hydroxyalkyl cellulose, sodium carboxymethyl cellulose, hydroxyethyl cellulose, hydroxypropyl cellulose, methylhydroxypropyl cellulose, methyl cellulose and ethylhydroxyethyl cellulose.

1 to 10% HPMC solid content of low to medium molecular weight (MW 10,000 to 40,000 Dalton). The viscosity can be enhanced with the addition of less than 1% p-benzoquinine. Similar antimicrobial and antifungal agents as those discussed in the above examples are used.

POLYACRYLAMIDE

Polyacrylamide, in a linear, branched chain, or crosslinked form can be used as a filling material in accordance with the present invention. As a preliminary matter, it has been found that commercially available material is not sufficiently pure, and therefore, purification is desired for the preferred embodiment.

PREPARATION AND PURIFICATION OF POLYACRYLAMIDE FOR USE IN VISCOELASTIC SOLUTIONS

Raw Materials:
Acrylamide, Electrophoresis Grade or other commercially available
  N, N'-methylenebisacrylamide
  Triethanol amine (TEA)
  Ammonium Persulfate
  Ammonium Sulfate
  Deionized Water (DI water), 12 MΩ or better
  Ethanol, USP Polymerization:
The polymerization is carried out in solution. The concentration is selected so that the resulting polymer solution is stirrable.

Acrylamide (and methylenebisacrylamide, or other crosslinking agent, if used) and ammonium sulfate are dissolved in DI water in a polymerization vessel. While stirring, the solution is charged with nitrogen and the vessel continuously purged with nitrogen to eliminate and exclude oxygen from the reaction. Ammonium persulfate and TEA are dissolved in DI water in separate containers and the solutions sparged with nitrogen. The reaction is initiated by adding the ammonium persulfate solution followed by the TEA solution without admitting oxygen to the reactor. The reaction may be run adiabatically or the temperature controlled by a heating or cooling bath. The polymerization is run essentially to completion, which typically requires several hours.

Precipitation:
The polymer is separated from the solution by precipitation with alcohol. Any lower alcohol may be used, but preferably ethanol is used. The precipitation may be carried out in the polymerization reactor, or the polymer solution transferred to a suitable vessel.

While stirring the solution, alcohol is added slowly until the polymer becomes insoluble and precipitates from solution. This occurs rapidly over a very narrow range of alcohol concentration. More alcohol is added to bring the slurry volume to about four times the initial solution volume and stirring continued for a period of time to allow the polymer particles to equilibrate with the alcohol water solution and firm up. The solid polymer is then collected on a filter. The polymer particles are then reslurried in alcohol and stirred for a period of time. The collection and reslurring is repeated. At this point, the polymer has previously been dried, but it would be more efficient to hold it as a slurry in alcohol.

Purification:
Most of the salts and unreacted monomer remained in the aqueous phase on precipitation of the polymer. The residual monomer is reduced to an acceptable level by extraction with water-alcohol solution.

Dry polymer powder or polymer filtered from alcohol-water slurry is placed into a beaker or other suitable vessel and slurried in alcohol water solution. The alcohol concentration is adjusted so that the polymer particles will be swollen, but will not agglomerate. After a period of time, the alcohol concentration is increased to firm up the particles for separation from the liquid on a filter. This process is repeated for four extraction cycles. The polymer particles are then slurried in an alcohol-water solution with the alcohol concentration adjusted so as to produce a desirable residual alcohol content in the dried polymer. The polymer is collected on a filter and dried.

Drying:
The mass of wet polymer is spread on glass trays and vacuum dried without heat. This typically requires two days. For larger volumes, a vacuum tumble dryer would be effective.

One aspect of the present invention relates to a new filling material which has good aesthetic properties, as measured by viscosity and elasticity, as well as good elimination properties. One embodiment of such a new filling material is a gel which comprises three components.

The first component is a water soluble polymer of hydrogel that is of high molecular weight distribution, above a renal threshold molecular weight of the polyacrylamide, and not eliminated rapidly through the kidneys upon subcutaneous release. Alternatively, the first component has a high molecular weight and is crosslinked. This component of the filling material is the minor polymeric component. However, it provides the majority of the physical properties of the filling material.

The second component of the filling material is a water-soluble polymer that has a molecular weight and a molecular weight distribution that is essentially under the renal threshold molecular weight of the polymer and is eliminated rapidly through the kidneys upon subcutaneous release. This component of the filling material is the major polymeric component. It provides enhanced radiolucency to the filler material and provides a synergistic viscosity effect with the first component.

The third component of this filling material is saline. Saline is used to dissolve the polymer and to adjust the osmolality of the polymer. In addition, a buffer may be added to the filling material to adjust the pH of the gel.

The utilization of such a composite gel as a filling material has the following advantages. The filling material of the present invention has a viscosity and an elasticity similar to that of a silicone gel. In addition, it has elimination properties that are similar to saline. In essence, the composite gel will, upon implantation, provide good aesthetic qualities while providing the assurance of safety after implantation because it can be quickly eliminated from the body upon the rupture of the shell. The composite gel further provides increased radioalucency.

The polymers used to make the composite gel can be any water soluble polymer or hydrogel. In a preferred embodiment, the first component is a polyacrylamide and the second component is a linear polyacrylamide. The first component of the gel may be a linear or a crosslinked polymer, and can range from approximately 1% to 9% of the total weight of the gel. The second component of the gel can range from approximately 4% to 36% of the total weight of the gel.

Several ideal compositions have been identified and their formulations are set forth below:

EXAMPLE A

| Component 1 | crosslinked polyacrylamide (~0.04% crosslinker) | 2.0 gm |
|---|---|---|
| Component 2 | linear polyacrylamide Mw = ~22,000 Daltons | 8.0 gm |
| Component 3 | saline and buffer | 90 gm |

This filler has a viscosity comparable to that of silicone gel and also will exhibit rapid elimination of about 98% of the gel into urine. The remaining 2% of the original gel may be eliminated through aspiration at the implantation site.

EXAMPLE B

A second example of the novel filler was made as follows:

| Component 1 | linear polyacrylamide Mw = ~6,000,000 Daltons | 5.0 gm |
|---|---|---|
| Component 2 | linear polyacrylamide Mw = ~22,000 Daltons | 20 gm |
| Component 3 | saline and buffer | 75 gm |

This filler has a viscosity comparable to that of silicone gel and also will exhibit rapid elimination of about 95% of the gel into the urine. The remaining 5% of the original gel may be eliminated by aspiration at the implantation site.

Another aspect of the present invention relates to a new sterilized filler. One embodiment of such a new sterilized filler comprises five components.

The first component of the sterilized filler is a crosslinked polyacrylamide. The second component of the sterilized filler is sodium citrate dihydrate which is a buffer salt. The third component of the sterilized filler is sodium dihydrogen phosphate dihydrate which is also a buffer salt. The fourth component of the sterilized filler is sodium chloride for osmolality. The fifth component of the sterilized filler is sodium bisulfite which is a viscosity stabilizer.

The properties of the sterilized filler are as follows:

Percent polymer: 4% viscosity: 130,000±30,000 cps @ 1 rad/sec

Molecular weight: Not applicable

PH: 7.2±0.5

Osmolality: 286±30 mOsmol/Kg $H_2O$

An example of the composition of the sterilized filler is as follows:

4% CPAM (a crosslinked polyacrylamide 0.179% sodium citrate dihydrate 0.106% sodium dihydrogen phosphate dihydrate 0.670% sodium chloride 0.050% sodium bisulfate As discussed earlier, commercially available polyacrylamide has been found to be insufficiently pure, and therefore purification is desired for the preferred embodiment.

Through the use of the composite gel as provided by the present invention, a filling material which has good aesthetic properties and good elimination properties may be provided. The filling material has a viscosity and an elasticity similar to that of a silicone gel. In addition, it has elimination properties that are similar to saline. In essence, the composite gel will provide good aesthetic qualities while providing the assurance of safety after implantation because it can be quickly eliminated from the body if the shell ruptures. The composite gel further provides increased radioaluceny.

It will be understood by person of ordinary skill in the art that many changes, additions, deletions and substitutions can be made to the present invention, the presently preferred embodiment of which is described herein, without departing from the spirit and scope of the present invention.

What is claimed is:

1. An implantable soft tissue prosthesis comprising:
    a hollow shell formed of a flexible elastomeric envelope, said shell having an inner volume and an exterior surface, said prosthesis being adapted to be surgically implanted such that the hollow shell thereof is adapted to retain a desired shape when filled with a filling material;
    said filling material comprising a gel or viscous liquid containing:
    a first polyacrylamide having a molecular weight distribution such that it is not eliminated through the kidneys upon subcutaneous release, having a solid content of such a formulation in the range of 2 to 20%, a viscosity in the range of 15,000 to 75,000 cps and a molecular weight range of the polyacrylamide in the range of 200,000 to 1.5 million, and
    a second polyacrylamide, which is a linear polyacrylamide having a molecular weight distribution such that it is eliminated rapidly through the kidneys upon subcutaneous release,
    said filling material having an osmolality in the range of 200 to 400 mOsm/kg.

2. The implant of claim 1, wherein the first polyacrylamide is selected from the group consisting of a linear polyacrylamide and a cross linked polyacrylamide.

3. The implant of claim 1 wherein the pH of said filling material is in the range of 6 to 8.

4. The implant of claim 1, wherein said filling material further comprises saline.

5. The implant of claim 1, wherein said filling material further comprises a buffer.

6. The implant of claim 1, wherein said filling material has a radiation penetration comparable with or better than that of 0.9% saline.

7. The implant of claim 1, wherein the filling material comprises 4% to 36% by weight of the second polyacrylamide, and saline.

8. The implant of claim 7 wherein the osmolality is 200 to 400 mOsm/kg.

9. The implant of claim 1 further comprising a lubricity agent.

10. An implantable soft tissue prosthesis comprising:
    a hollow shell formed of a flexible elastomeric envelope, said shell having an inner volume and an exterior surface, said prosthesis being adapted to be surgically implanted such that the hollow shell thereof is adapted to retain a desired shape when filled with a filling material;
    said filling material comprising a gel or viscous liquid containing a polymeric material selected from the group consisting of polyacrylamide and derivatives of polyacrylamide, said polymeric material having a solid content of such a formulation in the range of 2 to 20%, a viscosity in the range of 15,000 to 75,000 cps and a molecular weight in the range of 200,000 to 1.5 million;
    said filling material having an osmolality in the range of 200 to 400 mOsm/kg, and a radiation penetration comparable with or better than that of 0.9% saline.

11. The implant of claim 10, wherein said filling material comprises 1.0% to 9.0% by weight of crosslinked polyacrylamide.

12. The implant of claim 10, wherein said filling material comprises about 4% by weight of crosslinked polyacrylamide.

13. The implant of claim 10, further comprising sodium bisulfate.

14. The implant of claim 10, further comprising about 0.05% by weight of sodium bisulfate.

* * * * *